United States Patent [19]

Bollinger et al.

[11] Patent Number: 5,096,921

[45] Date of Patent: Mar. 17, 1992

[54] ORGANIC COMPOUNDS

[75] Inventors: Pietro Bollinger, Bottmingen; Hans U. Gubler, Köniz; Jörg Schnyder, Berne, all of Switzerland

[73] Assignee: Sandoz Ltd., Basle, Switzerland

[21] Appl. No.: 562,097

[22] Filed: Aug. 2, 1990

Related U.S. Application Data

[62] Division of Ser. No. 262,420, Oct. 25, 1988, Pat. No. 4,956,381.

[30] Foreign Application Priority Data

Oct. 26, 1987 [GB] United Kingdom ............. 8725009
Feb. 19, 1988 [GB] United Kingdom ............. 8803908
Aug. 26, 1988 [GB] United Kingdom ............. 8820347

[51] Int. Cl.$^5$ ............................................. A61K 31/38
[52] U.S. Cl. ........................................................ 514/443
[58] Field of Search ........................................ 514/443

[56] References Cited

U.S. PATENT DOCUMENTS 4,692,460 9/1987 Carson ............................. 514/443

Primary Examiner—Stanley J. Friedman
Attorney, Agent, or Firm—Gerald D. Sharkin; Robert S. Honor; Thomas O. McGovern

[57] ABSTRACT

α-[10-oxy-4H-benzo[4,5]cyclohepta[1,2-b]thiophen-4-ylidene]-carboxylic acids, or physiologically-hydrolysable and -acceptable esters or pharmaceutically acceptable salts thereof are useful for effecting monokine inhibition, in particular interleukin-1 release or secretion inhibition, as a therapeutic means other than anti-inflammatory or anti-pyretic means.

14 Claims, No Drawings

ORGANIC COMPOUNDS

This is a division of application Ser. No. 07/262,420, filed Oct. 25, 1988, now U.S. Pat. No. 4,956,381.

The present invention relates to a new use, in particular a new pharmaceutical use, for the compound group comprising α-[10-oxy-4H-benz[4,5]cyclohepta[1,2-b]thiophen-4-ylidene]-carboxylic acids, their physiologically-hydrolysable and -acceptable esters and their pharmaceutically acceptable salts, said compound group being referred to hereinafter collectively as COMPOUNDS OF THE INVENTION.

COMPOUNDS OF THE INVENTION are known and have been described together with processes for their production e.g. in European Patent Publication No. 0 138 765 A2 (=Application No. 84810475).

As described in European Patent Publication No. 0 138 765 A2, the 4H-benzo[4,5]cyclohepta[1,2-b]thiophene nucleus of COMPOUNDS OF THE INVENTION may bear substituents in addition to those specified at the 4- and 10- positions. In particular there may be further substitution in the benzene and/or in the thiophene ring. Thus apart from the substituents at the 4- and 10-positions, the 4H-benzo[4,5]-cyclohepta[1,2-b]thiophene nucleus may for example be substituted, e.g. mono-substituted, in the benzene ring by halogen, e.g. chlorine, or hydroxy.

One particular group of COMPOUNDS OF THE INVENTION described and claimed in European Patent Publication No. 0 138 765 A2 comprises compounds of formula Ia

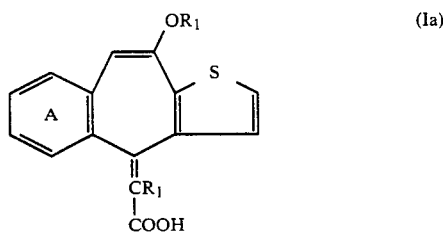

wherein
R$_1$ is hydrogen, C$_{1-4}$alkyl or phenyl-(C$_{1-4}$alkyl),
R$_2$ is hydrogen, or C$_{1-4}$alkyl, and
ring A is unsubstituted or halo- or hydroxy-substituted; and their physiologically-hydrolysable and -acceptable esters and their pharmaceutically acceptable salts.

In accordance with the teaching of European Patent Publication No. 0 138 765 A2, compounds of the above formula Ia wherein R$_1$ is C$_{1-4}$alkyl, R$_2$ is hydrogen and ring A is unsubstituted or mono-hydroxy or mono-halo (e.g. mono-chloro) substituted, preferably wherein ring A is unsubstituted, and their physiologically-hydrolysable and -acceptable esters and their pharmaceutically acceptable salts, form a preferred sub-group.

A further group of COMPOUNDS OF THE INVENTION is comprised by the [2-halo-10-oxy-4H-benzo[4,5]cyclohepta[1,2-b]thiophen-4-ylidene]-acetic acids, their physiologically-hydrolysable and -acceptable esters and their pharmaceutically acceptable salts, for example compounds of formula Ib

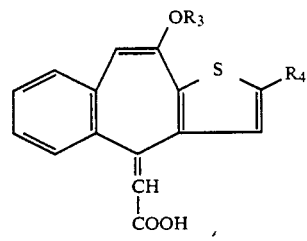

wherein
R$_3$ is hydrogen or C$_{1-4}$alkyl and
R$_4$ is halogen,
and their physiologically-hydrolysable and -acceptable esters and their pharmaceutically acceptable salts.

These are also known and have been described together with processes for their production in published UK Patent Publication No. 2 183 648 A and equivalents world-wide including e.g. German Patent Application No. 3641907.9.

In accordance with the teachings of said UK Patent Publication No. 2 183 648 A, compounds of the above formula Ib wherein R$_3$ is C$_{1-4}$alkyl and their physiologically-hydrolysable and -acceptable esters and their pharmaceutically acceptable acid addition salts, form a preferred sub-group.

Compounds of formula Ia and Ib, esters and salts as defined above as well as the above defined sub-groups thereof are also preferred as COMPOUNDS OF THE INVENTION for use in accordance with the present invention.

In the compounds of formula Ia and Ib, alkyl groups as R$_1$, R$_2$ and R$_3$ as well as alkyl moieties of phenyl-(C$_{1-4}$alkyl) groups as R$_1$ (in formula Ia) may be branched or straight-chain. When R$_1$ or R$_3$ is C$_{1-4}$alkyl, this is preferably methyl. By halogen as R$_4$ (in formula Ib) is meant fluorine, chlorine, bromine or iodine. Preferably R$_4$ is chlorine.

By the term "physiologically-hydrolysable and -acceptable esters", e.g. as applied compounds of formula Ia or Ib, is meant esters in which the carboxylic group is esterified and which are hydrolysable under physiological conditions to yield an alcohol which is itself physiologically acceptable, e.g. non-toxic, at desired dosage levels. Such esters include, e.g. esters with aliphatic alcohols having 1 to 4 carbon atoms.

Pharmaceutically acceptable salts, e.g. of compounds of formula Ia or Ib, include, e.g. alkali metal salts, such as the sodium and potassium salts, as well as alkaline earth metal salts, such as the calcium salts.

It will be appreciated that COMPOUNDS OF THE INVENTION wherein the 10-oxy group is 10-hydroxy, e.g. compounds of formula Ia or Ib wherein R$_1$ or R$_3$ is hydrogen, exist in both keto as well as in enol form, e.g. in the case of compounds of formula Ia and Ib as descried in European Patent Publication No. 0 138 765 A2 and UK Patent Publication No. 2 183 648 A. It is to be understood that, where tautomeric forms occur, the present invention embraces use of both keto and enol forms, i.e., in so far as COMPOUNDS OF THE INVENTION are defined herein, for convenience, by reference to the enol form only, the invention is not to be understood as being in any way limited by the particular nomenclature or graphic representation employed.

COMPOUNDS OF THE INVENTION, e.g. compounds of formula Ia or Ib, exist in both cis and trans isomeric forms, i.e. as Z and E isomers. The present invention is to be understood as embracing use of both individual cis and trans isomers as well as mixtures thereof. In the present specification and claims, cis (Z) and trans (E) isomers are designated in accordance with conventional CIP-nomenclature [Angew. Chem. 94, 614(1982) and Loc. cit.], as more closely explained e.g. in the aforementioned European Patent Publication No. 0 138 765 A2 and UK Patent Publication No. 2 183 648 A.

In general, for the purposes of the present invention, use of the (Z) isomers of COMPOUNDS OF THE INVENTION is preferred. For use in accordance with the invention, COMPOUNDS OF THE INVENTION are thus preferably in predominantly Z-isomeric form. Most preferably they are in pure or substantially pure Z-isomeric form.

Individual compounds suitable for use in accordance with the present invention are:

A) [10-Methoxy-4H-benzo[4,5]cyclohepta[1,2-b]thiophen-4-ylidene]-acetic acid ethyl ester [(Z,E)-isomer mixture].

B) [7-Chloro-10-methoxy-4H-benzo[4,5]cyclohepta[1,2-b]thiophen-4-ylidene]-acetic acid ethyl ester: B1) as the (Z,E)-isomer mixture; B2) as the (Z)-isomer; B3) as the (E)-isomer.

C) [6-Hydroxy-10-methoxy-4H-benzo[4,5]cyclohepta[1,2-b]thiophen-4-ylidene]-acetic acid ethyl ester: C1) as the (Z,E)-isomer mixture; C2) as the (Z)-isomer; C3) as the (E)-isomer.

D) [10-Methoxy-4H-benzo[4,5]cyclohepta[1,2-b]thiophen-4-ylidene]-acetic acid: D1) as the (Z,E)-isomer mixture; D2) as the (Z)-isomer; D3) as the (E)-isomer.

E) [10-Methoxy-4H-benzo[4,5]cyclohepta[1,2-b]thiophen-4-ylidene]-acetic acid methyl ester: E1) as the (Z,E)-isomer mixture; E2) as the (Z)-isomer; E3) as the (E)-isomer.

F) [7-Chloro-10-methoxy-4H-benzo[4,5]cyclohepta[1,2-b]thiophen-4-ylidene]-acetic acid: F1) as the (Z,E)-isomer mixture; F2) as the (Z)-isomer; F3) as the (E)-isomer.

G) [6-Hydroxy-10-methoxy-4H-benzo[4,5]cyclohepta[1,2-b]thiophen-4-ylidene]-acetic acid: G1) as the (Z,E)-isomer mixture; G2) as the (Z)-isomer; G3) as the (E)-isomer.

H) [10-Hydroxy-4H-benzo[4,5]cyclohepta[1,2-b]thiophen-4-ylidene]-acetic acid [(Z)-isomer].

J) [2-Chloro-10-methoxy-4H-benzo[4,5]cyclohepta[1,2-b]thiophen-4-ylidene]-acetic acid ethyl ester: J1) as the (Z,E)-isomer mixture; J2) as the (Z)-isomer; J3) as the (E)-isomer.

K) [2-Chloro-10-methoxy-4H-benzo[4,5]cyclohepta[1,2-b]thiophen-4-ylidene]-acetic acid: K1) as the (Z)-isomer; K2) as the (E)-isomer.

Preferred compounds for use in accordance with the present invention are compounds D2 and K1 above, especially compounds D2 and K1 in predominantly, more especially pure or substantially pure, Z-isomeric form.

As described in European Patent Publication No. 0 138 765 A2 and UK Patent Publication No. 2 183 648 COMPOUNDS OF INVENTION have, on the basis of observed activity in e.g. the adjuvant arthritis test in the rat, the lipopolysaccharide LPS induced fever test in the rat and the arthritis pain test in the rat, been found to be useful as anti-inflammatory, anti-pyretic and analgesic agents.

In accordance with the present invention it has now surprisingly been found that COMPOUNDS OF THE INVENTION exhibit monokine, in particular IL-1 (interleukin-1), inhibitory activity, in particular IL-1 release or secretion inhibitory activity. COMPOUNDS OF THE INVENTION have thus now been found to be useful for use in the treatment or supportive treatment of a wide range of further conditions or diseases not hitherto suspected. [For a general discussion of the rôle of IL-1 in the etiology of disease and other morbid conditions see e.g. Dinarello, J. Clin. Immunol. 5 (5), 287–297 (1985)].

In accordance with the particular findings of the present invention, the present invention provides, in a first aspect:

1. A method of effecting monokine inhibition, in particular IL-1 release or secretion inhibition as a therapeutic means other than anti-inflammatory or anti-pyretic means, in a subject in need thereof which method comprises administering to said subject an effective amount of a COMPOUND OF THE INVENTION.

In a series of specific or alternative embodiments, the present invention also provides:

2. A method of effecting monokine inhibition, in particular IL-1 release or secretion inhibition, as a therapeutic means other than anti-pyretic or anti-inflammatory means in or for the treatment of exogenous or endogenous insult in a subject in need thereof, which method comprises administering to said subject an effective amount of a COMPOUND OF THE INVENTION.

In a further or alternative embodiment the invention provides:

2.1 A method for the treatment of acute phase response other than pyretic or inflammatory response to exogenous or endogenous insult or for the treatment of acute phase changes other than pyretic or inflammatory changes consequent to occult infection or chronic illness in a subject in need thereof, which method comprises administering to said subject an effective amount of a COMPOUND OF THE INVENTION.

In a yet further or alternative embodiment the invention provides:

2.2 A method for the treatment of neutrophilia, mononuclear cellular infiltration, hyperemia, hypozincemia, hypoferremia, muscle proteolysis, anorexia or morbid somnolence, for example encountered in acute phase response to exogenous or endogenous insult or in acute phase changes consequent to occult infection or chronic illness in a subject in need thereof, which method comprises administering to said subject an effective amount of a COMPOUND OF THE INVENTION.

Examples of exogenous or endogenous insult include for example microbial invasion, e.g. bacterial or viral infection (such as influenza), adverse or morbid immunological reaction, neoplastic disturbance, burns or injury.

Examples of occult infection or chronic illness include, in particular, arthritis, especially rheumatoid arthritis and inflammatory bowel disease.

In a series of further specific or alternative embodiments, the present invention also provides:

3. A method of inducing or effecting immunosuppression, in particular for the treatment of autoimmune disease in a subject in need thereof, which method comprises administering to said subject an effective amount of a COMPOUND OF THE INVENTION.

Specific autoimmune diseases to which the above method is applicable include, for example: ankylosing spondylitis, autoimmune hematological disorders (including e.g. hemolyticodo anaemia, aplastic anaemia, pure red cell anaemia and odiopathic thrombocytopaenia), systemic lupus erythematosus, polychondritis, sclerodoma, Wegener granulamotosis, dermatomyositis, chronic active hepatitis, myasthenia gravis, psoriasis, idiopathic sprue, autoimmune inflammatory bowel disease (including e.g. ulcerative colitis and Crohn's disease), endocrine opthalmopathy, Grave's disease, sarcoidosis, multiple sclerosis, primary billiary cirrhosis, juvenile diabetes (diabetes mellitus type I), Reiter's syndrome, non infectious uveitis (anterior and posterior), autoimmune keratitis (including e.g. keratoconjunctivitis sicca and vernal keratoconjunctivitis), interstitial lung fibrosis, psoriatic arthritis and glomerulonephritis (with and without nephrotic syndrome, e.g. including idiopathic nephrotic syndrome or minimal change nephropathy), whereby underlined diseases are of particular interest.

For these purposes COMPOUNDS OF THE INVENTION may, if desired or as appropriate, be employed as adjunct or adjuvant to other immunosuppressive steroid or cyclosporin therapy, in particular therapy employing the immonosuppressive drug substance Ciclosporin or cyclosporin A (also known and commercially available as SANDIMMUNE ® or SANDIMMUN ®).

4. A method of treating a) tissue calcium depletion or b) degenerative processes in bone or cartilage in a subject in need thereof, which method comprises administering to said subject an effective amount of a COMPOUND OF THE INVENTION.

In a further or alternative embodiment the invention provides:

4.1 A method of treating bone decalcification or resorption (including calcium depletion in the bone matrix); or 4.2 A method of treating odontal or periodontal calcium deficiency; or 4.3 A method of treating resorptive processes (e.g. calcium resorption) or fibroblastic infiltration at or within bone joints, in a subject in need thereof, which method comprises administering to said subject, an effective amount of a COMPOUND OF THE INVENTION.

In a particular embodiment the invention provides a method as defined under 4 and 4.1 to 4.3 above for the treatment of tissue calcium depletion or degenerative process in bone or cartilage as component of periodontal disease, osteoarthritis and ankylosing spondylitis in particular as well as of any other disease, for example odontal or periodontal calcium deficiency; osteoporosis of varyious genesis, including, e.g. climacteric or postmenopausal osteoporosis, as well as osteoporosis consequential to old age, immobilization or trauma; osteopathy, including acute and chronic states associated with skeletal demineralisation; osteomalacia, e.g. as an adjuvant to specific therapy; bone healing and regeneration; as well astetany and latent tetany.

In view of their utility in modifying the processes of calcium resorption or bone calcium depletion, COMPOUNDS OF THE INVENTION are especially useful in the treatment of arthritic conditions in which such processes are a major factor, in particular the treatment of osteoarthritis and ankylosing spondylitis.

5. A method for the treatment of fibrosis or fibrotic conditions including, for example, congenital hepatic fibrosis, endomyocardial fibrosis, cystic fibrosis, diatomite fibrosis, pulmonary fibrosis, retroperitoneal fibrosis, neoplastic fibrosis, periuretic fibrosis, postfibrinous fibrosis, proliferative fibrosis, replacement fibrosis, fibrosis uteri, post-operative adhesion and scars in a subject in need thereof, which method comprises administering to said subject an effective amount of a COMPOUND OF THE INVENTION.

COMPOUNDS OF THE INVENTION are especially useful in the treatment of pulmonary fibrosis.

6. A method for the treatment, or supportive or adjunct treatment of tumour invasiveness or of symptoms associated with tumour growth (including muscle proteolysis), of Kreutzfeld-Jacob disease, of Alzheimer's disease, of morbid somnolence, of gout, of endotoxin shock or of epidermolysis bullosa in a subject in need thereof, which method comprises administering to said subject an effective amount of a COMPOUND OF THE INVENTION.

In the method of the invention as defined under 6 above, COMPOUNDS OF THE INVENTION are particularly useful for the treatment of symptoms associated with tumour growth (including muscle proteolysis), gout or endotoxin shock.

As alternatives to the above the present invention also provides:

A. A COMPOUND OF THE INVENTION for use in any method as defined under 1 to 6 above; or B. A COMPOUND OF THE INVENTION for use in the preparation of a pharmaceutical composition for use in any method as defined under 1 to 6 above.

C. A composition for use in any method as defined under 1 to 6 above comprising a COMPOUND OF THE INVENTION together with one or more pharmaceutically acceptable diluents or carriers therefor.

Utility of COMPOUNDS OF THE INVENTION as monokine inhibitors, in particular as IL-1 release or secretion inhibitors, as well as utility of COMPOUNDS OF THE INVENTION in treating diseases and conditions as hereinabove specified, may be demonstrated in standard pharmacological test methods as well as in clinic, for example in accordance with the methods hereinafter described.

1. IL-1 (INTERLEUKIN-1) SECRETION INHIBITION

1.1 Chondrocyte Test (Bioassay)

Introduction

Confluent rabbit chondrocyte cell cultures have proved to be relatively specific target cells for IL-1. Purified IL-1, [Schnyder et al., J. Immunol. 138, 496 (1987)], recombinant human IL-1-$\beta$ (rhIL-1) or conditioned media collected from stimulated human monocytes, mouse and rabbit peritoneal macrophages or mouse cell line P388D$_1$, [Koren et al., J. Immunol., 114, 894 (1975)] cause characteristic changes in the secretory pattern of chondrocytes. In particular, a latent metalloproteinase (MP) is induced, whilst secretion of plasminogen activator (PA) is reduced. The MP-response is relatively IL-1 specific, IL-2, TNF-$\alpha$, recombinant human $\alpha$-interferon (rh IFN-$\alpha$), rh IFN-$\gamma$, phorbol myristate acetate, concanavalin A, E-type-prostaglandin and indomethacin having no influence. Monokine-induced PA secretion reduction provides a highly sensitive parameter (comparable with the LAF-test - see below), though not as specific as that of MP. [c.f. Evêquoz et al., Biochem. J. 219 667–677 (1984); Schnyder et al., Brit. J. Rheumatol. 24 (Supp.1), 128–132 (1985); and Schnyder et al., J. Immunol. 138, 496–503 (1987)].

1.1.a Mouse Macrophage Monokine Inhibition

Resident mouse peritoneal macrophages [Schnyder et al., J. Exp. Med., 148, 435–450 (1978)] are cultivated in vitro for 1 day with test compound at varying concentrations. Culture media are diluted 1:1 (v:v) with fresh medium and added to confluent rabbit chondrocytes. MP activity in the chondrocyte culture medium is monitored after a further two days. COMPOUNDS OF INVENTION, in particular compound D2 are active in suppressing monokine release in the above test method at concentrations of from about 3.0 to about 100 $\mu$M. Thus a determined ED$_{50}$ for compound D2 in substantially pure Z-isomeric form in 3–5 separate experiments each run in triplicate is of the order of 100 $\mu$M.

1.1.b Human Monocyte Monokine Inhibition

Mononuclear cells are obtained from the blood of healthy volunteers via centrifugation and cultivated on tissue culture dishes with test compound at varying concentrations [Schnyder et al., J. Immunol., 138, 496–503 (1987)]. The non-adherent lymphocytes are removed after 4 hours by washing several times. Fresh medium, test compound and lipopolysaccharide (LPS) as stimulant are added and the monocytes incubated for further 19 hours. The pooled culture media are diluted 1:10 (v:v) with fresh medium and added to confluent rabbit chondrocytes. MP activity in the chondrocyte culture medium is assayed after a further 2 days.

COMPOUNDS OF THE INVENTION, in particular compounds D2 and K1, are active in suppressing monokine release in the above test method at concentrations of the order of from about 30 to about 100 $\mu$M. Thus determined ED$_{50}$s for the compounds D2 and K1 each in substantially pure Z-isomeric form in a series of 3 or 7 separate experiments each with 3 parallel determinations are, for both compounds, of the order of 60 to 100 $\mu$M.

1.2 LAF-TEST (Thymocyte proliferation)

Lymphocyte proliferation is the standard test for monokine activity. It is highly sensitive, though relatively unspecific, with IL-2, phorbol myristate acetate, concanavalin A, E-type-prostaglandin and indomethacin all effecting disturbance. Human monocyte culture media are prepared as described under 1.1.b. above, diluted 1:10, 1:20 and 1:40 (v:v), and added to $1.5 \times 10^{-6}$ thymocytes/ml (obtained from C3H/HeJ mice) Dulbecco's modified Eagle's medium, containing 20 mM hydroxyethyl-piperazin-ethanesulfonic acid, 12 mM NaHCO$_3$, 2 mM glutamine, 2% foetal bovine serum, 10 $\mu$M 2-mercaptoethanol, 0.1 $\mu$M indomethacin and antibiotics. The cells are incubated for 2 days in 96-well culture plates and the proliferation rate determined using a $^3$H-thymidine pulse (1 $\mu$C/well) during the final 6 hours. The incorporated radioactivity is collected on filter paper and counted. In the above test method, COMPOUNDS OF THE INVENTION inhibit monokine production in concentrations of the order of from about 30 to about 100 $\mu$M. Thus determined ED$_{50}$s for the compounds D2 and K1 each in substantially pure Z-isomeric form in a series of 2 separate experiments each with 3 parallel determinations are of the order of 30 $\mu$M.

In order to rule out an antagonistic effect or a direct influence of the COMPOUNDS OF THE INVENTION on the proliferation of mouse thymocytes which are used above in the LAF-test, the effect of the COMPOUNDS OF THE INVENTION on the incorporation of $^3$H-thymidine is determined after thymocyte stimulation with recombinant human IL-1 or IL-2. In this test model, the COMPOUNDS OF THE INVENTION, in particular compounds D2 and K1, are found to have no significant influence on 10 ng/ml recombinant human IL-2 or 75 ng/ml recombinant human IL-1 induced proliferation and no concentration dependency is detectable.

Furthermore the influence on IL-1 induced secretion of MP is determined using chondrocytes as a target system for IL-1. IL-1 (Genzyme Corporation, USA) is added with or without a COMPOUND OF THE INVENTION or Dexamethasone (control) to chondrocytes and the activity of metalloproteinase is determined in the supernatant media of 2 days incubation period. In this test method, COMPOUNDS OF THE INVENTION, in particular compounds D2 and K1, do not influence the IL-1 induced secretion of MP.

1.3 RIA-Kit. IL-1 Quantification

The procedures of example 1.1.b. above are repeated and IL-1 concentrations in recovered, undiluted culture medium determined employing a CISTRON IL-1 radioimmuno assay kit (the CISTRON kit is obtainable from Cistron, 10, Bloomfield Avenue, P.O. Box 2004, Pine Brook, NJ 07 058 USA. It is IL-1$\beta$ specific and recognises both intra- and extra-cellular material).

COMPOUNDS OF THE INVENTION, in particular compounds D2 and K1 are active in the above test method in suppressing determined extra-cellular IL-1 levels. In contrast determined intracellular IL-1 levels remain substantially unaffected. Thus determined ED$_{50}$s for extra-cellular IL-1 level suppression for the compounds D2 and K1 each in substantially pure Z-isomeric form in 2–8 experiments each with 3 parallel determinations are of the order of 40 and 25 $\mu$M respectively. In each determination therefrom, extra-cellular content is reduced significantly.

1.4 Release Versus Synthesis Inhibition

1.4.a Preparation of Homogenates and Lysates 0.3 ml Phosphate-buffered saline, containing 1% heat-inactivated AB-human serum, is added to washed adherent human monocytes and the cells are detached using a rubberpoliceman. The solution containing the cells is then transferred to two other wells belonging to the same group. This procedure is repeated three times. The final pooled suspension (0.9 ml) is homogenized using a Dounce homogenizer (Kontes Co, Vineland, NJ) by five times 7 strokes with the B-pestle.

The lysate is prepared by adding to the washed human monocyte monolayers 0.3 ml 0.01% digitonin in water.

1.4.b Effect on IL-1 Synthesis and Release

50 $\mu$l homogenate is diluted to 500 $\mu$l with medium and added to confluent chondrocytes to monitor the metalloproteinase inducing activity as a measure of IL-1 content.

The content of IL-1 was also determined in the culture media and the cell homogenates and cell lysates using the RIA-test (see 1.3.).

In these tests, COMPOUNDS OF THE INVENTION, in particular compound D2, significantly reduce the levels of IL-1 in the supernatant media, while the mean cellular content of IL-1 both in the homogenates and lysates is only slightly reduced or remains unchanged.

1.5 Effect on Monocyte Adherence

Monocytes of freshly harvested human mononuclear cells are prepared in presence of the compound to be tested or a vehicle. After 4 h the medium is aspirated and the cell monolayer is washed as usual. The adherent monocytes are then lysed using digitonin in water, and the amount of DNA and the activity of the cytosol enzyme LDH is measured. In this test neither the COMPOUNDS OF THE INVENTION, in particular compound D2, nor the vehicle reduce the adherence of the monocytes.

1.6 Effect on the Secretion of Monokines

Besides IL-1, TNF-α and IL-6 are two well recognized monokines that are released from stimulated monocytes.

Culture media from human monocytes are prepared as described above. The IL-1 and TNF-α content is monitored by the RIA-test, IL-6 by bioassay as disclosed below. COMPOUNDS OF THE INVENTION, in particular compound D2, inhibit the release of IL-1 in a more significant rate than that of IL-6 and TNF-α.

IL-6 Bioassay

To measure IL-6 in conditioned media from human monocytes, $2.4 \times 10^4$ cells/ml B13.29 in 0.2 ml are cultured on 96-well plates (Costar) for 48 h with culture media, diluted in serum free Iscove's modified Dulbecco's medium supplemented with 200 U/ml of recombinant IL-6, 50 μM 2-mercaptoethanol and antibiotics. The proliferation rates are determined using a $^3$H-thymidine pulse (1 μC/well) during the final 6 h. The incorporated radioactivity is collected on filter paper, counted and related to a standard preparation of IL-6.

1.7 Effect on the Leakage of Lactate dehydrogenase and on the Secretion of Lysozyme Culture media from human monocytes are prepared as disclosed above. Lysozyme and lactate dehydrogenase (LDH) are monitored kinetically by using a Twinreader (Flow Laboratories AG) linked to a personal computer. Samples (50 μl) for LDH are mixed with 200 μl substrate mixture, containing in final concentrations 50 mM phosphate buffer, pH 7.5, 0.8 mM sodium pyruvate, 0.24 mM NADH$_2$ and 0.04% bovine albumin and the changes in absorbance at 340 nm are measured 11 times at 1-min intervals. The computer calculates the initial velocities which are used to determine the units. Samples (50 μl) for lysozyme are mixed with 100 μl suspension of 1.2 mg/ml M. Lysodeikticus in 67 mM phosphate buffer pH 6.2 and the changes in turbidity at 492 nm monitored 11 times at 4-min intervals. With every assay series, a calibration curve is made with crystalline hen egg-white lysozyme [J. Schnyder et.al., J. Exp. Med. 148, 435 (1978)]. No significant leakage of LDH from control and treated cell cultures is observed. COMPOUNDS OF THE INVENTION, in particular compound D2 reduces the release of lysozyme only marginally and not under the level of unstimulated controls.

2. PREVENTION OF BONE RESORPTION (TREATMENT OF TISSUE CALCIUM DEPLETION)

Calvaria halves (frontal and parietal parts) from 4–5 day Swiss albino mice are cultured on stainless steel grids in BGJ bone tissue culture medium, supplemented with 1 mg/ml BSA at the interphase of medium and gas in a humidified atmosphere (95% air/5% $CO_2$) at 37° C.—c.f. Reynolds et al. in "Organ Culture in Biomed. Res." eds. Balls and Mamichendam, Cambridge University Press, p.p. 355-366 (1976).

Influence of test substance at varying concentrations on calcium release into the test medium in the presence of calcium release stimulators [PGE$_2$, LPS or 1,25 dihydro vitamin D$_3$ (1,25D$_3$)] is determined. For this purpose calcium concentrations are measured in bone culture supernatants obtained from 72 and 144 hour cultures and in TCA extracts of the calvaria at the end of culture by spectrometric methods [Gindler et al., Am. J. Clin. Pathol. 58, 376–382 (1972)]. Activity of lysosomal enzyme N-acetyl-glucose-aminidase in bone culture supernatants and in Triton 100 extracts of calvaria after culture is also determined employing the method of Banerjee and Basu, Biochem. J., 45, 113–118 (1975). Changes in enzyme activity are expressed as μ units/-calvarium half and as % release.

COMPOUNDS OF THE INVENTION, e.g. compound D2 or K1 in substantially pur Z-isomeric form, inhibit calcium release and exhibit concomitant influence on N-acetyl-glucose-aminidase in the above test methods at concentrations of the order of from $1 \times 10^{-5}$ and $5 \times 10^{-6}$M. Determined IC$_{50}$ values for compound D2 in substantially pure Z-isomeric form are for example as follows:

| | IC$_{50}$ (M) | |
| --- | --- | --- |
| In the presence of: | Calcium | N-acetylglucose-aminidase |
| PGE$_2$ | $2.2 \times 10^{-5}$ | $7.9 \times 10^{-6}$ |
| LPS | $2.8 \times 10^{-5}$ | $8.3 \times 10^{-6}$ |
| 1,25D$_3$ | $3.8 \times 10^{-5}$ | $3.7 \times 10^{-5}$ |

(For the calculation of IC$_{50}$ values the difference between resorption rate in control cultures and resorption in maximally stimulated cultures is taken as 100%. The IC$_{50}$ is taken as the concentration of test substance which inhibits maximum resorption by 50%).

3. DISEASE MODIFYING ACTIVITY IN AN ANIMAL MODEL OF RHEUMATOID ARTHRITIS

Following induction of adjuvant arthritis in 48 adult female rats, the test compound is administered orally for 40 days. Articular swelling and bone densitometry are measured at days 10, 20, 30 and 40 and compared with control animals receiving placebo. In addition, cartilage glycosaminoglycans (GAG) are measured in femoral condyles removed on completion of the treatment period. α$_2$-Macroglobulin is determined in serum on days 0, 3, 6, 9, 16 and 22.

On administration of the COMPOUNDS OF THE INVENTION at a dosage rate of from 2.5 to 20 mg/kg/day/p.o., after an initial reduction of bone density caused by the inflammatory process, gradual restoration of normal mineral content is observed. Not only does the bone density increase as indicated by the densitometric measurements according to the method disclosed below, but also the serum $\alpha_2$-macroglobulin concentrations are reduced in a dose dependent manner. Furthermore, analysis of the GAG content of affected cartilage reveals a dose-related increase of proteoglycan content.

In this test model of rheumatoid arthritis, COMPOUNDS OF THE INVENTION, e.g. compound D2 is substantially pure Z-isomeric form, exhibit disease modifying activity especially after a period of 30 days treatment, in particular they show a protective effect on cartilage and bone in rats with adjuvant arthritis.

The procedure for in vivo estimation of bone density in adult rats as used in the above test method is based on the radiographic densitometric method described by Albanese et al. in J. Amer. Ger. Soc. 17, 142–153 (1969). A longitudinal bone survey is conducted in the arthritic rats during the treatment with the test substance and compared with untreated arthritic rats and control aminals. In vivo quantitative radiographic scanning is performed taking the trabecular mass as the parameter. The radiographic picture is then scanned and grey values are converted into Relative Optical Density (ROD) units by means of a high resolution densitometric device. Because of the characteristics of the system (image darkening representing increased Relative Optical Density) the recorded values are expressed as $(1-x)$ where x is the experimentally measured ROD in order to conform to the biological effect of X-rays on bone tissue (i.e. film darkening indicates decrease in bone density). The resulting densitometric values are plotted in dependency of weight of the animal, the animal groups being selected within the same weight range.

4. IMMUNOSUPPRESSIVE ACTIVITY (AUTOIMMUNE DISEASES)

In each of the following test methods test compound, i.e. COMPOUND OF THE INVENTION, e.g. compound D2 or K1 each in substantially pure Z-isomeric form, is administered at a dosage rate of from ca. 5 to 60 mg/kg/day/p.o. either alone or in conjunction with cyclosporin A at a dosage rate of from ca. 1 to 10 mg/kg/day/p.o. in olive oil (i.e. substantially below dosages commonly required for immunosuppressive efficacy in the described test models).

4.1 UVEITIS: Modulation of Experimental Autoimmune Uveitis (EAV)

Testing is carried out in accordance with the general methodology described by Nussenblatt et al. in Arch. Ophthal. 100, 1146–1149 (1982). Groups of 6 to 10 Lewis (♀) rats weighing ca. 150–200 g are immunized with 30 μg of bovine S antigen emulsified (1:1 p.p.w.) in complete Freund's adjuvant enriched with 2.5 mg/ml *Mycobacterium tuberculosis* H 37 RA, by injection into the hind foot pad.

Test substance is administered at dosages indicated above administered either i) in the absence of or ii) together with cyclosporin A therapy on 7 consecutive days commencing 7 days after immunization. Control groups receive placebo in place of test substance. The rats are killed on the 14th day following immunization and the eyes are removed immediately, fixed in formaldehyde, embedded in parafin wax and stained with heamatoxylin-eosin and PAS. Histopathologic evaluation is preformed in masked fashion and inflammation graded on a scale of from 0 (no inflammation) to 4 (panophthalmitis). Selected cases are examined by transmission and scanning electron microscopy. Eyes from animals exhibiting EAV show generalised inflammation of the retina and choroid with inflammatory cells enmeshed in a fibrinous exudate occurring in the vitreous cavity, subretinal space and anterior chamber.

On administration of (i) test compound or (ii) test compound plus cyclosporin A at dosages indicated, substantial reduction in the number of animals evidencing EAV is observed compared with results for control groups receiving (i) placebo or (ii) placebo plus cyclosporin A at the same dosage.

4.2a MULTIPLE SCLEROSIS I: Preventive Activity in Experimental Allergic Encephalomyelitis (EAE)

Testing is carried out in accordance with the general methodology described by Borel et al. in Agents and Actions, 6, 468 (1976). EAE is induced in groups of 8 to 12 Wistar (♀) or Lewis (♂) rats each weighing 150 to 200 g by intradermal injection into each hind foot pad of 0.1 ml of an emulsion comprising 2.5 g bovine spinal cord (lyophylised and reconstituted with 12 ml $H_2O$), 1.5 ml Arlacel A, 8.0 ml Nujol and 0.2 ml saline containing 20 mg killed, dried *Mycobacterium phlei*. (i) Test compound or (ii) test compound plus cyclosporin A are administered 5 days a week, commencing on the day of sensitisation and continuing for 3 weeks. Onset of EAE in control groups generally commences between 9 and 16 days after sensitisation and is marked by symptoms of paralysis in the hind limbs and tail. Test animals are examined daily for the symptoms of the disease and disease occurrence is scored as positive when complete involvement of both hind legs and the tail is observed. The test animals are kept under observation for a total period of 25 days.

On administration of (i) test compound or (ii) test compound plus cyclosporin A at dosages indicated above, substantial reduction of occurrence of EAE is observed over the test period in comparison with occurrence in control groups receiving (i) placebo or (ii) placebo plus cyclosporin A at the same dosage.

4.2.b MULTIPLE SCLEROSIS II: Activity in Established EAE

Testing is carried out analogously to 4.2.a but with administration of (i) test substance or (ii) test substance plus cyclosporin A commencing on day 8 to day 9 after sensitisation (i.e. immediately prior to appearance of disease symptoms), with administration daily or every 2nd day, and continuing for ca. 14 days. During the treatment period animals are examined daily for symptoms of the disease, and scored as under 4.2.a.

On administration of (i) test substance or (ii) test substance plus cyclosporin A at dosages indicated above substantial reduction of appearance of EAE disease symptoms is observed over the test period in comparison with appearance in control groups receiving (i) placebo or (ii) placebo plus cyclosporin A at the same dosage.

4.3 SYSTEMIC LUPUS ERYTHEMATOSUS: (NZB/NZW)F1 mouse model

Trials are based on the (NZB/NZW)F1 mouse strain as described and discussed by Steinberg et al. in Bulletin on the Rheumatic Diseases 28, nos. 4–5, 940–946 (1977–78) published by The Arthritis Foundation, Atlanta, Ga. Females of this strain spontaneously develop characteristic of the SLE syndrome including formation of anti-DNA and anti-erythrocyte autoantibodies as well as proteinuria at age ca. 5 to 7.5 months. The condition ultimately leads to death.

For the purpose of the trial groups of 6 to 8 ♀ mice are employed. Treatment with (i) test substance or (ii) test substance plus cyclosporin A administered 5× weekly and continuing for ca. 8 to 10 weeks commences a) prior to spontaneous development of autoantibodies, e.g. at ca. 5 months' age or b) subsequent to spontaneous development of autoantibodies, e.g. at ca. 8-9 months' age. Anti-DNA and anti-erythrocyte antibody titres are measured at regular intervals during the trial period employing ELISA technique and during the trial period commencing from ca. 1 week prior to commencement of therapy. Additional parameters subject to control are development of proteinuria (measured 1×/week) and life span. Results in groups treated as under (a) and (b) above indicate prophylactic and therapeutic effectiveness respectively.

On administration of (i) test substance or (ii) test substance plus cyclosporin A at dosages indicated above, substantial reduction of autoantibody titres and occurrence of proteinuria as well as an increase in average life span are observed in both prophylactic and therapeutic treatment regimens as compared with results for control groups receiving (i) placebo or (ii) placebo plus cyclosporin A at the same dosage.

5. PULMONARY FIBROSIS

Testing is carried out in accordance with the general methodology described by G. J. Laurent et al. in Eur. J. Clin. Invest. (1981) 11, 441–448. Pulmonary fibrosis is induced in groups of 4 New Zealand white rabbits (aged 127 days at commencement of the experiment), each weighing 2.0–2.5 kg, by intratracheal instillation of 10 mg/kg bleomycin. The lungs of test animals are examined 2, 4 and 8 weeks later. On administration of test compound, i.e. COMPOUND OF THE INVENTION, e.g. compound $D_2$ or $K_1$ each in substantially pure Z-isomeric form, at a dosage rate of from ca. 2.5 to 60 mg/kg/day/p.o., substantial reduction of pulmonary fibrosis is observed in comparison with control groups receiving placebo.

6. CLINICAL TRIAL I: PSORIASIS

The trial is conducted employing adult ♂ and ♀ subjects exhibiting chronic severe psoriasis involving 20% or more of the body surface as estimated by the rule of nines, and whose disease condition is either stable or progressive on current therapy. All systemic, topical or phototherapy specifically directed at skin disease is stopped for at least 2 week prior to commencement of the trial. Only bland emollients, 2% salicylic acid in olive oil, coal tar shampoos, and/or 1% hydrocortisone cream or ointment and medication for arthritis or other concomitant disease to psoriasis is continued during this period.

After the 2-week "wash out" period, subjects are admitted to the trial after an overnight fast of 8-10 hours. On admission, the following laboratory tests are performed: complete blood-count, serum electrolytes, glucose, calcium, phosphorous, uric acid, ALT-/AST/LDH (alanine amino transferase/aspartate aminotransferase/lactate dehydrogenase), plasma epidermal growth factor, growth hormone and urine EGF. Clinical extent of psoriasis is estimated by rule of nines, and lesions are graded for redness, thickness and scaliness using a 0–4 scale as described by Kragballe et al. Arch. dermatol. 119, 548–552 (1983). Clinical photographs are taken of selected lesions. A 6 mm punch skin biopsy is performed using 1% lidocaine infiltration anaesthesia.

During the course of the trial, subjects receive COMPOUND OT THE INVENTION, e.g. compound $D_2$ or $K_1$, each in substantially pure Z-isomeric form, at dosages of from ca. 400 to ca. 1200 mg/p.o./day administered once or in divided dosages up to 4× daily.

No other therapy is allowed during the trial period, except as already employed during the "wash out" period. All testing carried out at entry into the trial (fasting blood, urine, estimation of clinical extent of sporiasis, clinical photography, punch skin biopsy) is repeated during the course of the trial on days 7, 14, 21 and 28.

Subjects taking part in the trial and receiving therapy in accordance with the invention exhibit marked improvement in psoriatic condition as evidenced by progressive reduction in clinical extent of psoriasis, in particular in the extent of sporiatic lesion, as well as by marked reduction in grading for lesion condition. In addition results from sequential punch skin biopsies indicate marked histological change in relation to lesion condition, including reduction of mitotic index, reduction of inflammatory infiltrate and noticeable improvement in vasculature.

Efficacy may also be proven on repetition of the trial in double blind, cross-over formal employing two groups of patients, one group receiving COMPOUND OF THE INVENTION in accordance with the above indicated regimen and the other receiving placebo only, both groups being matched for extent of lesions.

7. CLINICAL TRIAL II: ALZHEIMER'S DISEASE (AD/SDAT)

The trial is carried out employing test groups comprising 6 to 10 subjects (♂ and ♀) identified as exhibiting mild to moderate dementia of the AD/SDAT type in accordance with parameters defined in DSM-III (Diagnostic and Statistical Manual of Mental Disorders, 3rd-edition), and excluding subjects exhibiting severe cardiovascular disease, hypotension (systolic B.P. <120), severe endocrine disease, severe liver disease, renal insufficiency and/or malabsorption syndrome.

The trial commences with an EEG and psychometric test at time 0. Subjects then receive placebo, or test medication administered as described below, and the EEG and psychometric tests are repeated 60, 120 and 180 minutes subsequent to administration.

Psychometric tests employed include:

i) The Selective Reminding Test/Buschke: "Selective Reminding for Analysis of Memory and Learning", J. Verbal Learning and Verbal Behaviour 12, 543-550 (1973);

ii) Measurement of Constructional Ability (Muratomo et al.: "Effect of Physiostigmin on Constructional and Memory Tasks in Alzheimer's disease," Arch. Neurol. 36, 501–503 (1973); and iii) Memory of Geometric Figures (Benton revised visual retention test).

During the course of the trial, subjects receive either a placebo or a COMPOUND OF THE INVENTION, e.g. compound $D_2$ or $K_1$, each in substantially pure Z-isomeric form, at dosages of from ca. 450 to ca. 1200 mg/p.o. administered once or in divided dosages 2 or 3×.

The following additional parameters are monitored:

Haematology: R.B.C., HB, HCT, W.B.C., differential counts, sedimentation rate, blood glucose.
Urine: Albumin, glucose.
Serum: Alkaline phosphatase, ALT, AST, S-GT, S-bilirubin, S-T4, S-T3, S-TSH, creatinin.

Subjects receiving COMPOUND OF THE INVENTION in the above indicated dosages exhibit marked improvement in condition as evidenced by EEG results and the results of psychometric tests as compared with subjects receiving placebo.

8. CLINICAL TRIAL III: CALCIUM RESORPTION—PERIODONTAL DISEASE

The trial is carried out employing volunteer subjects (♂ and ♀) exhibiting periodontal disease. COMPOUND OF THE INVENTION, e.g. compound D2 or K1 in substantially pure Z-isomeric form, is administered at dosages of from ca. 400 to 1200 mg/p.o./day administered once or in divided dosages up to 4× daily, or by injection into the gum at the site of disease at dosages of the order of about 0.5 or 1.0 to about 5.0 mg into each gum pouch. The subjects are examined at regular weekly or 2× weekly intervals for disease progression. Subjects are found to exhibit marked improvement in condition after ca. 2 to 3 weeks continuous therapy.

9. CLINICAL TRIAL IV: DEGENERATIVE JOINT DISEASE

The trial is carried out employing volunteer subjects ♂ and ♀) exhibiting either psoriatic arthritis or seronegative spondylarthrosis or osteoarthrosis. COMPOUND OF THE INVENTION, e.g. compound D2 or K1 in substantially pure Z-isomeric form, is administered at dosages of from ca. 200 to 1200 mg/p.o./day, once or in divided dosages up to 4× daily for 8 weeks. The subjects are examined at a regular interval of 2 weeks for disease progression on parameters such as pain sensation at the joints, evaluation of the functional capacity according to Steinbrocker, hand grip strength or Richtie Index. Subjects are found to exhibit improvement in condition after the 8 week treatment period.

Equivalent results may be obtained in trials performed in relation to other diseases and conditions hereinbefore specified (e.g. involving muscle proteolysis, morbid somnolence etc.) employing COMPOUNDS OF THE INVENTION, in particular compounds D2 or K1, each in substantially pure Z-isomeric form, at the same or equivalent dosage levels to those described above.

Daily dosages required in practicing the method of the present invention will, of course, vary depending on a variety of factors, for example the particular COMPOUND OF THE INVENTION chosen, the particular condition to be treated and the effect desire. In general however satisfactory results are achieved on administration of COMPOUNDS OF THE INVENTION at daily dosage rates of the order of ca. 100 mg up to ca. 2.0 g, preferably ca. 350 mg up to ca. 2.0 g, up to ca. 1.5 g administered p.o. 1×/day or in divided doses 2 to 4× daily, or in retard form. Suitable unit dosage forms for oral administration thus comprise from ca. 25 mg to ca. 1.0 g active ingredient together with one or more pharmaceutically acceptable diluents or carriers therefor.

Where COMPOUNDS OF THE INVENTION are administered in conjunction with, e.g. as an adjuvant to, other immunosuppressive therapy, e.g. for the treatment of specific diseases or conditions as hereinabove specified, dosages for the co-administered immunosuppressant will of course vary depending on the type of immunosuppressant drug employed, e.g. whether it is a steroid or a cyclosporin, on the specific drug employed, on the condition to be treated, the therapy desired and so forth. In general however, satisfactory results may be obtained on administration of the co-administered immunosuppressive drug at dosages of the order of 80% e.g. 50% of those commonly required when the said co-administered immunosuppressive drug is employed as mono-therapy. Thus where a cyclosporin is employed as co-administered immunosuppressant satisfactory results are obtained on administration in a dose range of from about 1 to about 25 mg/kg/day (e.g. in the case of cyclosporin A, from about 5 to about 15 mg/kg/day), administered to the patient orally once or in divided doses 2 to 3×/day. Where i.v. administration of a cyclosporin is required, e.g. administration by infusion (for example, in the initial phase of treatment), lower dosages, e.g. of the order of from about 0.5 to about 5.0 mg/kg/day (e.g. in the case of cyclosporin A, from about 1 to about 3 mg/kg/day for an initiating dose, or to about 2 mg/kg/day for a maintainance dose) are generally indicated.

In accordance with the foregoing the present invention provides, in a yet further aspect:

7. A method of reducing the dosage of an immunosuppressant drug, for example an immunosuppressant steroid or immunosuppressant cyclosporin, e.g. cyclosporin A, required for the effective treatment of a subject receiving immunosuppressant therapy, for example for the treatment of any disease or condition treatable by immunosuppressant therapy hereinbefore set forth, which method comprises co-administration of an effective amount of a COMPOUND OF THE INVENTION, e.g. at dosages as hereinbefore described; or as well as 8. A method for effecting immunosuppression, e.g. for treating any of the specific auto-immune diseases hereinbefore set forth, in a subject in need of such treatment which method comprises administering to said subject an effective amount of a) A COMPOUND OF THE INVENTION and b) a second drug substance, said second drug substance being an immunosuppressant drug, for example an immunosuppressant steroid or immunosuppressant cyclosporin, e.g. cyclosporin A.

The composition for use according to the invention may be prepared by bringing a COMPOUND OF THE INVENTION into intimate admixture with the pharmaceutically acceptable diluents or carriers and effecting formulation or presentation so as to provide for or permit convenient administration.

The following is illustrative of the preparation of solid compositions in accordance with the invention.

EXAMPLE

Production of Solid Compositions for Oral Application

Tablets or capsules may contain the active agent in admixture with conventional pharmaceutically acceptable excipients, e.g. inert diluents, such as calcium carbonate, sodium carbonate, lactose and talc, granulating and disintegrating agents, e.g. starch and alginic acid, flavouring, colouring and sweetening agents, binding agents, e.g. starch, gelatin and acacia, and lubricating agents, e.g. magnesium stearate, stearic acid and talc.

The following example is illustrative for the preparation of capsule forms:

| INGREDIENTS | WT/DOSE |
|---|---|
| Active ingredients, e.g. Compound D2 or K1 above in substantially pure Z-isomeric form | 200.00 mg |
| Lactose (200 mesh) | 109.75 mg |
| Corn Starch | 35.00 mg |
| Silicon dioxide (Aerosil 200) | 1.75 mg |
| Magnesium stearate | 3.50 mg |
| Total | 350.00 mg |

The active ingredients are intimately admixed employing conventional galenic procedures, filled into hard gelatin capsules and the capsules sealed. Capsule weight=97.0 mg: Total weight for filled capsule=447.0 mg.

COMPOUNDS OF THE INVENTION are well tolerated at dosages required for use in accordance with the present invention.

Thus established $LD_{50}$ values for the compound D2 in substantially pure Z-isomeric form in mice and rats after 14 days p.o. and 7 days i.v. are: in mice, p.o. 1623 mg/kg, i.v. 163 mg/kg; in rats, p.o. 1721 mg/kg, i.v. 50 mg/kg.

In beagle dogs the same compound is found to be generally well tolerated when administered at high dose levels of up to 200 mg/kg/day for 26 weeks.

For compound K1 in substantially pure Z-isomeric form, in pilot toxicological studies in the beagle dog, no pathological effects are observed on administration of doses of 150 and 200 mg/kg/p.o. in gelatine capsules over 5 weeks and in olive oil from week 6 to week 8 on.

Pharmaceutically acceptable acid addition salt forms exhibit the same or similar levels of tolerability/activity as free acids.

What is claimed is:

1. A method of inducing or effecting immunosuppression, treating exogenous or endogenous insult, or treating fibrosis or fibrotic conditions in a subject in need of said treatment which comprises administering to said subject a therapeutically effective amount of a α-[10-oxy-4H-benzo[4,5]cyclohepta[1,2-b]thiophen-4-ylidine]-carboxylic acid, or a physiologically-hydrolysable and -acceptable ester or a pharmaceutically acceptable salt thereof.

2. A method of inducing or effecting immunosuppression, treating exogenous or endogenous insult, or treating fibrosis or fibrotic conditions in a subject in need of said treatment which comprises administering to said subject a therapeutically effective amount of a α-[10-oxy-4H-benzo[4,5]cyclohepta[1,2-b]thiophen-4-ylidine]-carboxylic acid of formula (Ia)

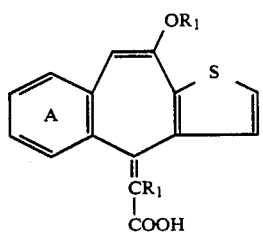

(Ia)

wherein
$R_1$ is hydrogen, $C_{1-4}$alkyl, or phenyl-($C_{1-4}$alkyl),
$R_2$ is hydrogen or $C_{1-4}$alkyl, and
ring A is unsubstituted or halo- or hydroxy-substituted;
or of formula (Ib)

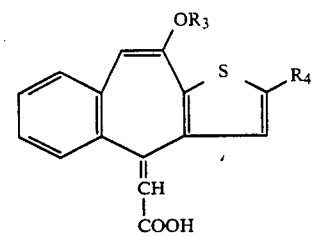

(Ib)

wherein
$R_3$ is hydrogen or $C_{1-4}$alkyl and
$R_4$ is halogen,
or a physiologically-hydrolysable and -acceptable ester or a pharmaceutically acceptable salt thereof.

3. A method according to claim 2 of treating bacterial or viral infection.

4. A method according to claim 2 of treating Reiter's syndrome.

5. A method according to claim 2 of treating non-infectious uveitis.

6. A method according to claim 2 of treating autoimmune keratitis.

7. A method according to claim 2 of treating psoriasis.

8. A method according to claim 2 of treating pulmonary fibrosis.

9. A method according to claim 2 in which 100 mg to 2.0 g of a compound of formula Ia or Ib or a physiologically-hydrolysable and -acceptable ester or a pharmaceutically acceptable salt thereof is administered daily.

10. A method according to claim 2 in which 25 mg to 1.0 g of a compound of formula Ia or Ib or a physiologically-hydrolysable and -acceptable ester or a pharmaceutically acceptable salt thereof is administered per unit dose.

11. A method according to claim 2 wherein the α-[10-oxy-4H-benzo[4,5]cyclohepta[1,2-b]thiophen-4-ylidene]-carboxylic acid or physiologically-hydrolysable and -acceptable ester thereof is a compound selected from A) [10-Methoxy-4H-benzo[4,5]cyclohepta[1,2-b]thiophen-4-ylidene]-acetic acid ethyl ester
B) [7-Chloro-10-methoxy-4H-benzo[4,5]cyclohepta[1,2b]thiophen-4-ylidene]-acetic acid ethyl ester
C) [6-Hydroxy-10-methoxy-4H-benzo[4,5]cyclohepta[1,2-b]thiophen-4-ylidene]-acetic acid ethyl ester
D) [10-Methoxy-4H-benzo[4,5]cyclohepta[1,2-b]thiophen-4-ylidene]-acetic acid
E) [10-Methoxy-4H-benzo[4,5]cyclohepta[1,2-b]thiophen-4-ylidene]-acetic acid methyl ester
F) [7-Chloro-10-methoxy-4H-benzo[4,5]cyclohepta[1,2-b]-thiophen-4-ylidene]-acetic acid
G) [6-Hydroxy-10-methoxy-4H-benzo[4,5]cyclohepta[1,2-b]-thiophen-4-ylidene]-acetic acid
H) [10-Hydroxy-4H-benzo[4,5]cyclohepta[1,2-b]thiophen-4ylidene]-acetic acid
J) [2-Chloro-10-methoxy-4H-benzo[4,5]cyclohepta[1,2-b]-thiophen-4-ylidene]-acetic acid ethyl ester
K) [2-Chloro-10-methoxy-4H-benzo[4,5]cyclohepta[1,2-b]-thiophen-4-ylidene]-acetic acid or a pharmaceutically acceptable salt thereof.

12. A method according to claim 2, wherein the α-[10-oxy-4H-benzo[4,5]cyclohepta[1,2-b]thiophen-4- ylidene]-carboxylic acid is [10-methoxy-4H-benzo[4,5-]cyclohepta[1,2-b]thiophen-4-ylidene]-acetic acid or a pharmaceutically acceptable salt thereof.

13. A method according to claim 2, wherein the α-[10-oxy-4H-benzo[4,5]cyclohepta[1,2-b]thiophen-4-ylidene]-carboxylic acid is [2-chloro-10-methoxy-4H-benzo[4,5]cyclohepta[1,2-b]-thiophen-4-ylidene]-acetic acid or a pharmaceutically acceptable salt thereof.

14. A method according to claim 2, wherein the α-[10-oxy-4H-benzo[4,5]cyclohepta[1,2-b]thiophen-4-ylidene]-carboxylic acid or physiologically-hydrolysable and -acceptable ester or pharmaceutically acceptable salt thereof is in pure or substantially pure cis form.

* * * * *